(12) United States Patent
Hong et al.

(10) Patent No.: US 8,980,827 B2
(45) Date of Patent: Mar. 17, 2015

(54) MEDICINAL COMPOSITION CONTAINING ECHINOCANDIN ANTIFUNGAL AGENT MICAFUNGIN AND PREPARATION METHOD AND USE THEREOF

(75) Inventors: Yunhai Hong, Shanghai (CN); Ying Xue, Shanghai (CN); Xiaoming Ji, Shanghai (CN)

(73) Assignee: Shanghai Techwell Biopharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 13/982,872

(22) PCT Filed: Jan. 31, 2012

(86) PCT No.: PCT/CN2012/070784
§ 371 (c)(1),
(2), (4) Date: Aug. 22, 2013

(87) PCT Pub. No.: WO2012/103801
PCT Pub. Date: Aug. 9, 2012

(65) Prior Publication Data
US 2013/0331312 A1    Dec. 12, 2013

(30) Foreign Application Priority Data

Jan. 31, 2011 (CN) .......................... 2011 1 0034055

(51) Int. Cl.
*A61K 38/12* (2006.01)
*A61K 9/00* (2006.01)
*A61K 9/19* (2006.01)
*A61K 47/26* (2006.01)

(52) U.S. Cl.
CPC ............... *A61K 38/12* (2013.01); *A61K 9/0019* (2013.01); *A61K 9/19* (2013.01); *A61K 47/26* (2013.01)
USPC ........................................ 514/3.6; 514/21.1

(58) Field of Classification Search
None
See application file for complete search history.

(56) References Cited

U.S. PATENT DOCUMENTS 6,774,104 B1    8/2004  Sawai et al.
2002/0160942 A1* 10/2002  Larew et al. ..................... 514/8

FOREIGN PATENT DOCUMENTS

| CN | 1315865 A | 10/2001 |
| CN | 1345333 A | 4/2002 |
| CN | 1179748 C | 12/2004 |
| CN | 100352495 C | 12/2007 |

OTHER PUBLICATIONS

International Search Report, from International Application PCT/CN2012/070784, dated Apr. 5, 2012, 5 pages.
Written Opinion of International Searching Authority, from International Application PCT/CN2012/070784, dated Apr. 5, 2012, 7 pages.
"Research progress of application of trehalose in medical field", Cheng et al., Medical Journal of Qilu, Aug. 2010, vol. 25, No. 4, pp. 374-376.
"Is trehalose special for preserving dry biomaterials?", Crowe L M, et al., Biophysical Journal, Oct. 1996, vol. 71, pp. 2087-2093.
"Why is trehalose an exceptional protein stabilizer?" Kaushik et al., The Journal of Biological Chemistry, Jul. 2003, vol. 278, No, 29, pp. 26458-26465.

* cited by examiner

*Primary Examiner* — Jeffrey E Russel
(74) *Attorney, Agent, or Firm* — Hamre, Schumann, Mueller & Larson, P.C.

(57) ABSTRACT

The present invention provides a medicinal composition containing micafungin or a pharmaceutically acceptable salt thereof and trehalose as a stabilizing agent.

12 Claims, 4 Drawing Sheets

MEDICINAL COMPOSITION CONTAINING ECHINOCANDIN ANTIFUNGAL AGENT MICAFUNGIN AND PREPARATION METHOD AND USE THEREOF

FIELD OF THE INVENTION

The present invention relates to a pharmaceutical composition for treating and/or preventing infectious diseases. Particularly, the present invention relates to a pharmaceutical composition containing the compound of Formula I or a pharmaceutically acceptable salt thereof and a pharmaceutically acceptable stabilizing agent, such as trehalose. Said composition is a lyophilized composition.

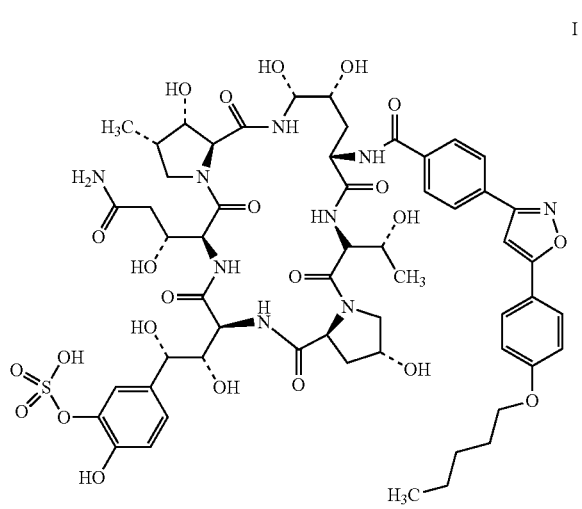

I

BACKGROUND OF THE INVENTION

The compound of Formula I is cyclic polypeptide compound, i.e., Micafungin. Following Caspofungin, Micafungin Sodium (FK463, Tradename: Mycamine; Fujisawa Co.) is the second echinocandin antifungal medicament approved by FDA, the structure of which is shown in Formula III. Micafungin is obtained by chemically modifying the fermentation product of *Coleophoma empedrit*. Micafungin was firstly marketed in Japan in 2002, and approved by FDA and marketed in US in May 2005. Clinical test has demonstrated that Micafungin is very efficient for treating *Candida* and *Aspergillus*, and can be used as first-line medicine for treating diseases caused by *Candida* infections.

Since Micafungin and the salts thereof are generally unstable to light, heat, humidity, acid, and the like, it is urgent to develop a pharmaceutical composition for stabilizing the compound and the salts thereof. CN 1179748C has disclosed a stable pharmaceutical composition of Micafungin in lyophilized form comprising lactose as stabilizing agent. CN 100352495C has disclosed a stable pharmaceutical composition of Micafungin in lyophilized form comprising maltose as stabilizing agent. However, both of the pharmaceutical compositions are not ideal in stability. The inventors have unexpectedly discovered that compared with both of the above compositions, the pharmaceutical composition of compound of Formula I comprising trehalose as stabilizing agent is by far stable.

The composition provided by the present invention is a safe, stable and reproducible lyophilized formulation, and can be directly used to treat/prevent infectious diseases.

SUMMARY OF THE INVENTION

In the study on the chemical stability of echinocandin antifungal compound, Micafungin, the inventors have tested various stabilizing agents, including sucrose, lactose, maltose and trehalose, and also the relationship between the content of stabilizing agent and the stability of a composition comprising Micafungin. The inventors have unexpectedly discovered that the chemical stability of the composition using trehalose as stabilizing agent is by far superior to that of other compositions using other stabilizing agents, especially the formulation using maltose as stabilizing agent disclosed in CN 100352495C and the formulation using lactose as stabilizing agent disclosed in CN 1179748C, regardless of the presence of additional pH regulators. Thus, the inventors have completed the present invention.

A pharmaceutical composition is provided by the invention, comprising:
a) the compound of Formula I or a pharmaceutically acceptable salt thereof, and
b) a pharmaceutically acceptable amount of stabilizing agent, trehalose.

Preferably, the stabilizing agent in the composition provided by the invention is trehalose. The weight ratio of stabilizing agent, trehalose to the compound of Formula I is 100:1-1:20, preferably, 20:1-1:5.

The pharmaceutical composition provided by the invention can be prepared as lyophilized powder by lyophilization. The lyophilized powder can be redissolved using aqueous solution as parenterally, preferably intravenously applicable liquid composition.

Preferably, said aqueous solution is sterile 0.9% sodium chloride injection (optionally comprising sterile water for injection), 5% glucose injection, bacteriostatic water for injection comprising methyl p-hydroxybenzoate and/or propyl p-hydroxybenzoate and/or 0.9% benzyl alcohol, or Ringer solution and/or lactate Ringer solution.

In an embodiment, the pharmaceutical composition of the invention comprises the pharmaceutically acceptable salts of compound of Formula I, i.e., Micafungin, as pharmaceutically active ingredient, and pharmaceutically acceptable stabilizing agent, i.e., trehalose, in suitable form and/or efficiently forming lyophilized cake, comprising or not comprising any additional pH regulator.

Moreover, the composition of the invention can comprise another, for example one or more, pharmaceutically acceptable stabilizing agent, including diluents or carriers well-known in the art, all of which are suitable for the compositions intended to be parenterally administrated, such as injectable formulations for intramuscular, subcutaneous, intravenous, intraperitoneal, or intramuscular administration. Such stabilizing agent includes, for example antioxidant, tonicity-adjusting agent, preservative, carbohydrate, wax, water-soluble and/or swellable polymer, hydrophilic or hydrophobic material, gelatin, oil, solvent, water, and the like.

Suitable solvents or diluents include (but not limited to) aqueous solvent, preferably, bacteriostatic water for injection comprising methyl p-hydroxybenzoate and/or propyl p-hydroxybenzoate and/or 0.9% benzyl alcohol, or normal saline or physiological saline, for example, 0.9% sodium chloride solution, or 0.45% or 0.225% sodium chloride solution, or Ringer solution and/or lactate Ringer solution. These solvents and/or diluents can be further used to redissolve the composition of the invention in the form of lyophilized powder, and/or to further dilute the redissolved solution thus obtained.

In another aspect, a method for preparing the pharmaceutical composition comprising the compound of Formula I is provided, said method comprising the following steps:

a) dissolving the stabilizing agent, i.e., trehalose in water or the solution comprising optional pH regulator;

b) adding the compound of Formula I or a pharmaceutically acceptable salt thereof, and dissolving them;

c) filtering the solution obtained in step b) and lyophilizing the solution.

In the solution obtained in step a), the concentration of stabilizing agent, i.e., trehalose is 10 mg/ml-500 mg/ml, preferably, 20 mg/ml-400 mg/ml.

In the solution obtained in step b), the concentration of compound of Formula I or the pharmaceutically acceptable salts thereof is 5 mg/ml-200 mg/ml, preferably, 10 mg/ml-150 mg/ml, more preferably, 40 mg/ml-100 mg/ml.

Moreover, the use of the composition according to the invention is provided, for preparing medicaments, preferably intravenous medicaments for preventing and/or treating fungal infections or diseases caused by *Candida* and/or *Aspergillus* and/or *Pneumocystis jirovecii* in mammalian, preferably human.

As used herein, the term "Micafungin" and the pharmaceutically acceptable salts thereof have been described in U.S. Pat. No. 6,774,104B1. Preferably, the pharmaceutically acceptable salt of Micafungin is sodium Micafungin.

SPECIFIC MODE FOR CARRYING OUT THE INVENTION

Comparative Example 1

Figure 1:
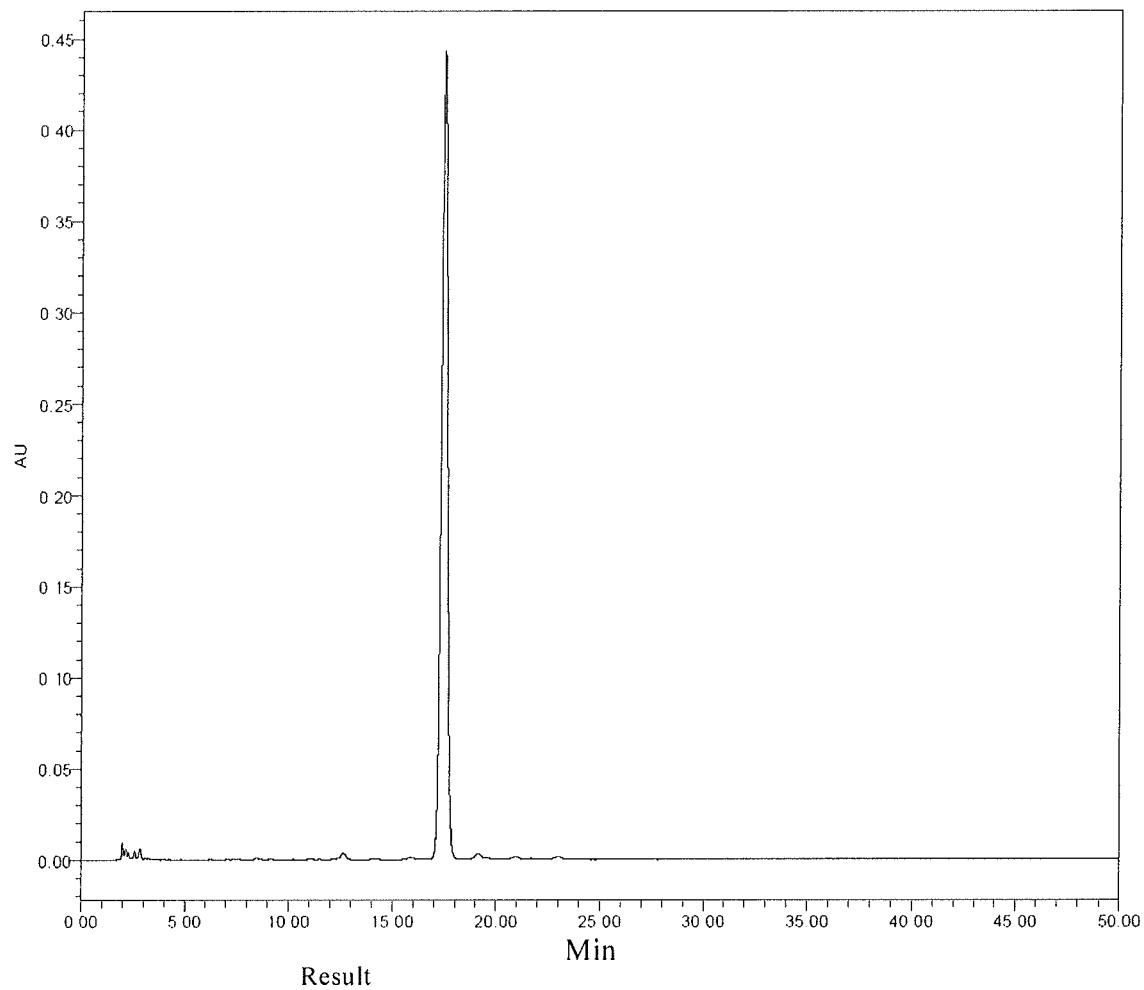
FIG. 1 is the HPLC pattern for Formulation 1 in Example at 0 day under the temperature of 70° C.

A composition was prepared according to Example 1 of CN 100352495C. Formulation 1 is listed as follows:

| | | |
|---|---|---|
| Sodium Micafungin | 2.5 g | |
| Lactose | 20 g | |
| Anhydrous citric acid | q.s. | |
| Sodium hydroxide | q.s. | |

Lactose was dissolved in pure water (200 ml) with heating at the temperature less than 50° C., The lactose solution was cooled to the temperature below 20° C., and then sodium Micafungin was added with gentle agitating to avoid producing bubbles. 2% aqueous solution of citric acid (0.95 ml) was added, 0.4% aqueous sodium hydroxide solution (about 2.4 ml) was added into the resulting solution for adjusting pH to 5.5, and then the solution was diluted using pure water, thereby obtaining specified volume (250 ml). The resulting solution was loaded into 100 vials (10 ml) with each containing 2.5 ml solution. The solution in each vial was lyophilized using freeze dryer according to conventional method, thereby obtaining the lyophilized compositions each comprising 25 mg of sodium Micafungin.

The resulting lyophilized preparation was stored at 70° C., and the residue of Micafungin was tested after 4 weeks.

Comparative Example 2

Lyophilized compositions each comprising 25 mg of sodium Micafungin (Formulation 2) were prepared according to example 1, except using 15 g of maltose instead of lactose.

The same stability test was performed on the resulting lyophilized preparation as comparative example 1.

Example 3

Preparation of Micafungin Formulation

The procedure for preparing the formulation is: dissolving the stabilizing agent, i.e., trehalose in water or the solution comprising optional pH regulator; adding the compound of Formula I or the pharmaceutically acceptable salts thereof, dissolving them, and determining the volume to a certain value; and lyophilizing the obtained solution.

Different formulations were obtained by changing the concentration of sodium Micafungin and/or trehalose and pH of the pH regulator. The formulations of each composition before lyophilized are shown in the following table:

| Formulation Number | Sodium Micafungin mg/ml | trehalose mg/ml | pH regulator (pH) | Weight ratio of trehalose to sodium Micafungin |
|---|---|---|---|---|
| 3 | 10 | 200 | None | 20:1 |
| 4 | 10 | 100 | None | 10:1 |
| 5 | 50 | 400 | None | 8:1 |
| 6 | 100 | 20 | None | 1:5 |
| 7 | 200 | 10 | None | 1:20 |
| 8 | 200 | 5 | None | 1:40 |
| 9 | 20 | 200 | 25 mM acetate (pH 5.5) | 10:1 |
| 10 | 20 | 200 | 25 mM phosphate (pH 5.5) | 10:1 |
| 11 | 20 | 200 | 25 mM phosphate (pH 6.0) | 10:1 |

After each formulation was lyophilized, the same stability test was performed as comparative example 1.

Example 4

Comparison for Stability of Micafungin Formulation

After the stability tests were applied to the samples from comparative example 1, comparative example 2 and example 3, the active ingredient was analyzed by HPLC. HPLC conditions included:

analytical column: YMC-Pack ODS-A column; spec.: 250×4.6 mm, S-5 µm, 1.2 nm;

column temperature: 35° C.;

detection: 210 nm;

mobile phase: amyl cyanide-phosphate buffer (pH 3.0) [dissolving sodium dihydrogen phosphate (16.56 g) and sodium perchlorate (7.73 g) by adding water, diluting the resulting solution to 1000 ml, and adjusting pH to 3.0 using diluted phosphoric acid (1→10)] (45:70). The content of Micafungin was calculated according to external standard method.

Results for stability test of composition after stored for 4 weeks at 70° C. are shown in the following table:

| Formulation number | 0 day | | | 70° C., 4 weeks | |
|---|---|---|---|---|---|
| | Appearance | Moisture % | Residue % | Appearance | Residue % |
| 1 | White, massive | 1.01 | 100 | White, massive | 87.6 |
| 2 | White, massive | 0.97 | 100 | White, massive | 85.7 |
| 3 | White, massive | 1.17 | 100 | White, massive | 98.9 |
| 4 | White, massive | 1.20 | 100 | White, massive | 98.9 |
| 5 | White, massive | 1.41 | 100 | White, massive | 98.7 |
| 6 | White, massive | 0.92 | 100 | White, massive | 98.0 |
| 7 | White, massive | 0.89 | 100 | White, massive | 91.5 |
| 8 | White, massive | 0.83 | 100 | White, massive | 77.9 |
| 9 | White, massive | 1.23 | 100 | White, massive | 98.8 |
| 10 | White, massive | 1.08 | 100 | White, massive | 98.7 |
| 11 | White, massive | 1.13 | 100 | White, massive | 98.8 |

Figure 2:
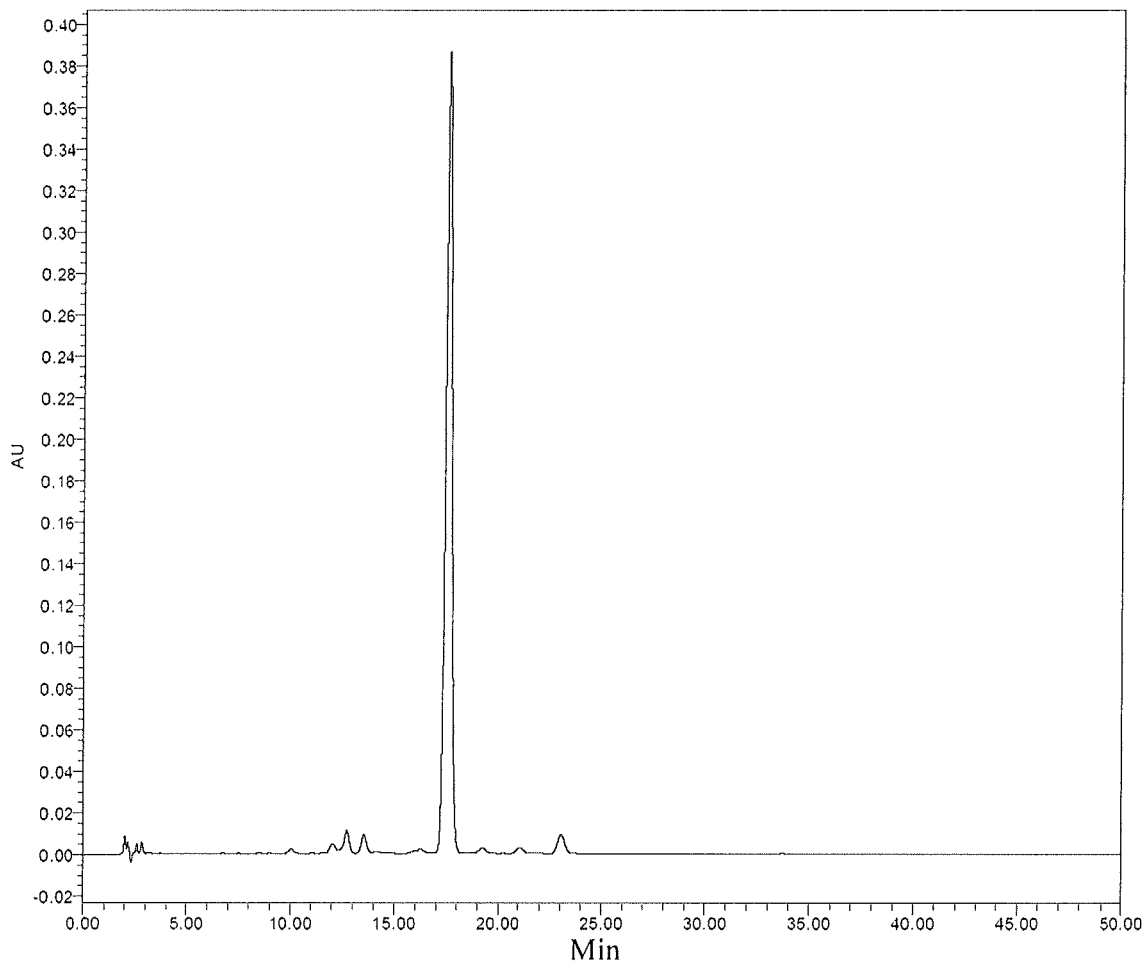
FIG. 2 is the HPLC pattern for Formulation 1 in Example after stored for 4 weeks under the temperature of 70° C.
Figure 3:
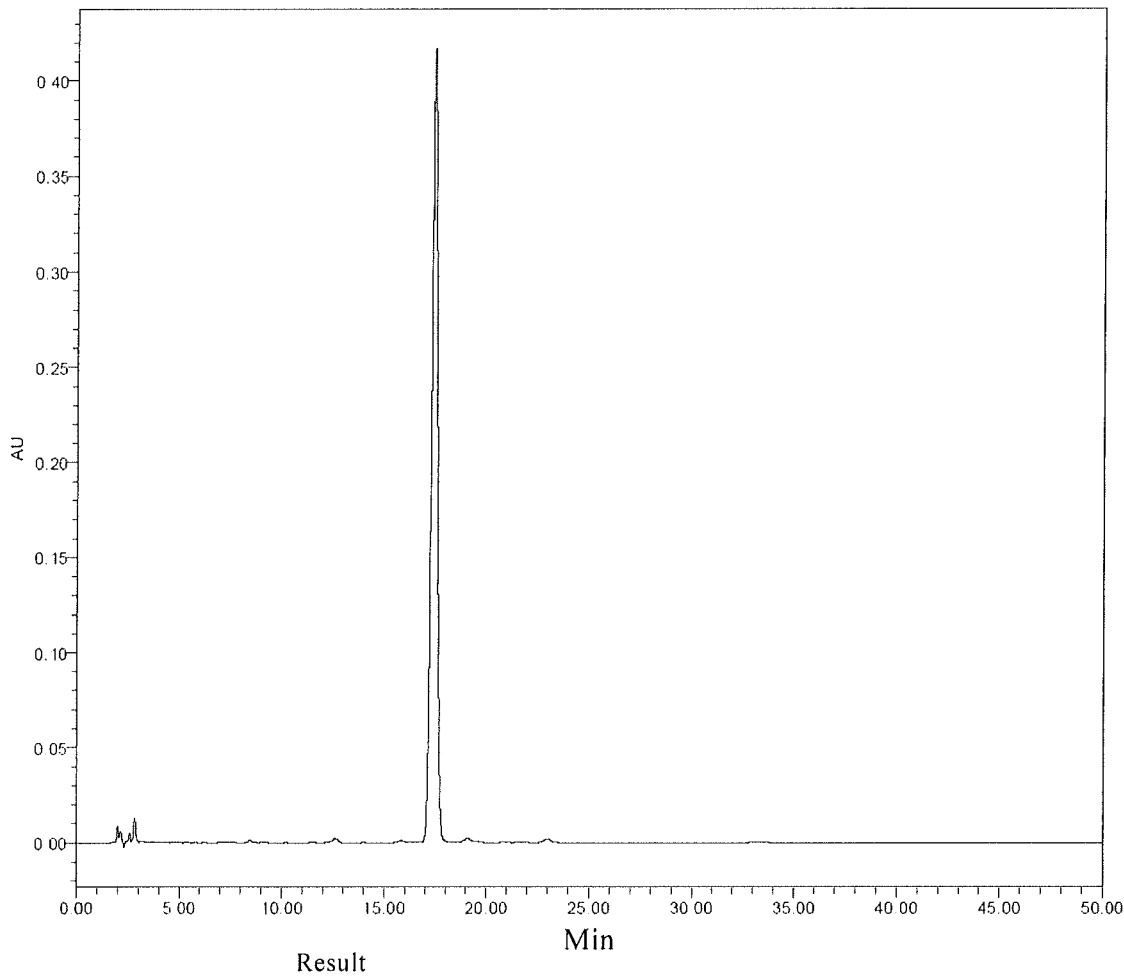
FIG. 3 is the HPLC pattern for Formulation 3 in Example at 0 day under the temperature of 70° C.
Figure 4:
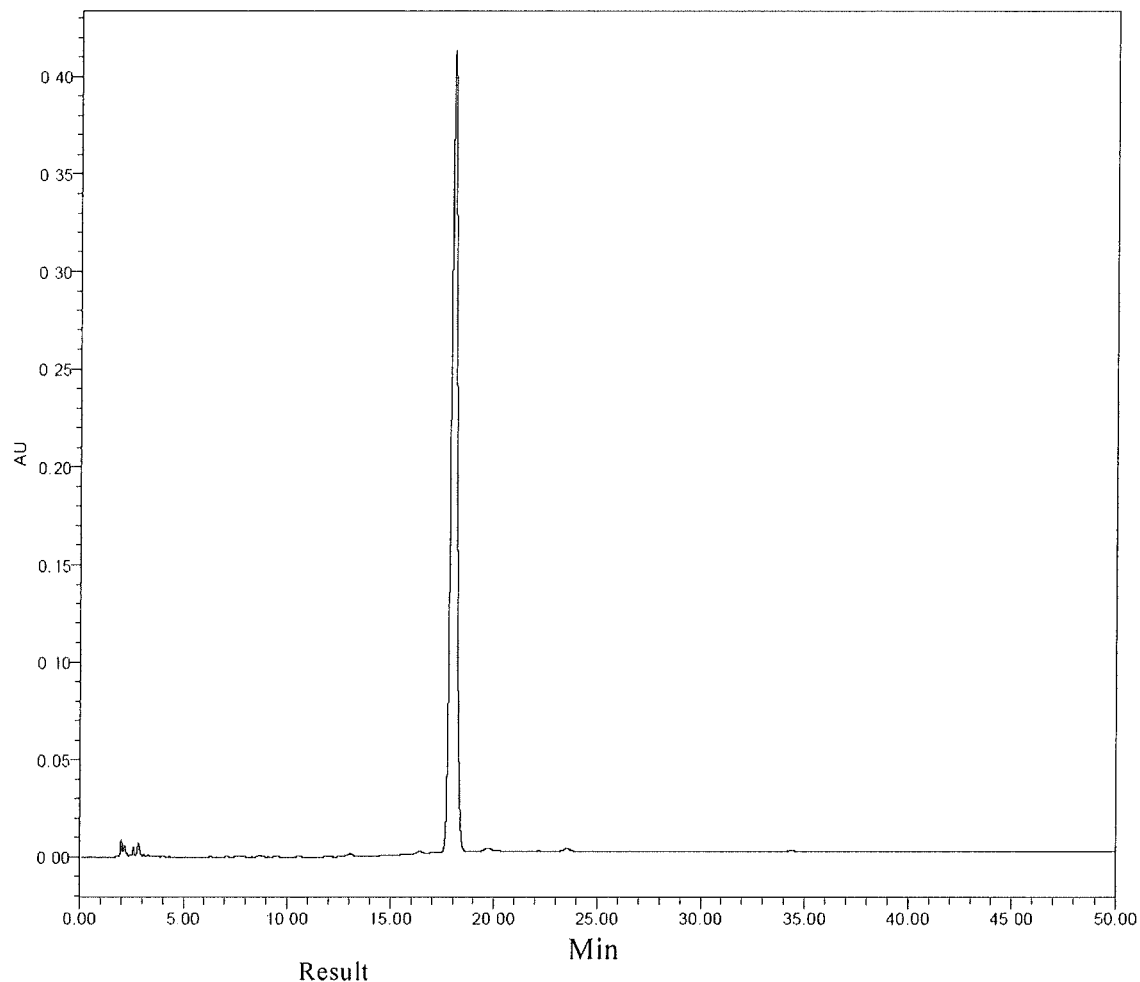
FIG. 4 is the HPLC pattern for Formulation 3 in Example after stored for 4 weeks under the temperature of 70° C.

It can be seen from the above table, compared with the formulations using lactose or maltose as stabilizing agent, the formulations using trehalose as stabilizing agent obviously have better stability, especially the formulations wherein the weight ratio of trehalose to sodium Micafungin is 100:1-1:20, preferably, 20:1-1:5. FIGS. 1-4 show the HPLC analytical patterns for formulations 1 and 3.

The invention claimed is:

1. An anti-fungi pharmaceutical composition, wherein said composition comprises:
   a) a pharmaceutically effective amount of a compound of Formula I or a pharmaceutically acceptable salt thereof; and
   b) a pharmaceutically acceptable amount of a stabilizing agent, trehalose

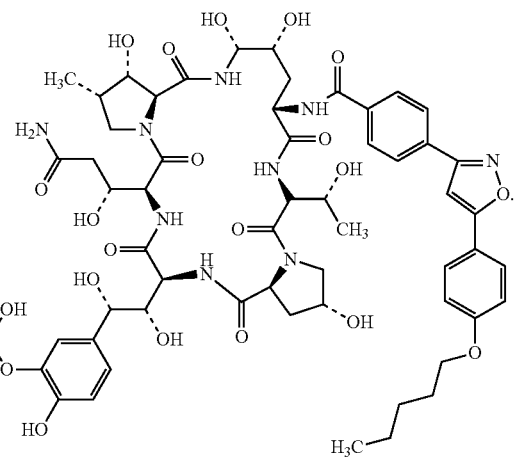

2. The pharmaceutical composition according to claim 1, wherein said composition is a lyophilized formulation.

3. The pharmaceutical composition according to claim 1, further comprising an additional pH regulator.

4. The pharmaceutical composition according to claim 1, wherein the weight ratio of the stabilizing agent, trehalose to the compound of Formula I or the salt thereof is 100:1-1:20.

5. The pharmaceutical composition according to claim 4, wherein the weight ratio of the stabilizing agent, trehalose to the compound of Formula I or the salt thereof is 20:1-1:5.

6. A preparation method for the pharmaceutical composition according to claim 1, comprising:
   a) dissolving the stabilizing agent, trehalose in water or a solution including a pH regulator;
   b) dissolving the compound of Formula I or the pharmaceutically acceptable salt thereof in the solution obtained in step a);
   c) filtering the solution obtained in step b); and
   d) lyophilizing the solution obtained in step c).

7. The preparation method according to claim 6, wherein in the solution obtained in step a), the concentration of the stabilizing agent, trehalose is 10 mg/ml-500 mg/ml.

8. The preparation method according to claim 7, wherein in the solution obtained in step a), the concentration of the stabilizing agent, trehalose is 20 mg/ml-400 mg/ml.

9. The preparation method according to claim 6, wherein in the solution obtained in step c), the concentration of the compound of Formula I or the pharmaceutically acceptable salt thereof is 5 mg/ml-200 mg/ml.

10. The preparation method according to claim 9, wherein in the solution obtained in step c), the concentration of the compound of Formula I or the pharmaceutically acceptable salt thereof is 10 mg/ml-150 mg/ml.

11. The preparation method according to claim 9, wherein in the solution obtained in step c), the concentration of the compound of Formula I or the pharmaceutically acceptable salt thereof is 20 mg/ml-100 mg/ml.

12. A method of using the composition according to claim 1, comprising:
   treating infectious diseases with the composition according to claim 1 in a subject in need thereof.

* * * * *